US009631868B2

(12) United States Patent
Kettner et al.

(10) Patent No.: US 9,631,868 B2
(45) Date of Patent: Apr. 25, 2017

(54) DENTAL FURNACE HAVING A COMBINED DISPLAY AND OPERATING DEVICE

(71) Applicant: Ivoclar Vivadent AG, Schaan (LI)

(72) Inventors: Philipp Kettner, Rankweil (AT); Robert Grünenfelder, Eschen (LI); Rudolf Wachter, Schaan (LI)

(73) Assignee: Ivoclar Vivadent AG, Schaan (LI)

( * ) Notice: Subject to any disclaimer, the term of this patent is extended or adjusted under 35 U.S.C. 154(b) by 383 days.

(21) Appl. No.: 14/173,177

(22) Filed: Feb. 5, 2014

(65) Prior Publication Data

US 2014/0236342 A1  Aug. 21, 2014

(30) Foreign Application Priority Data

Feb. 19, 2013  (DE) .................. 10 2013 101 633

(51) Int. Cl.
| G05B 11/01 | (2006.01) |
| B29C 39/00 | (2006.01) |
| G06F 19/00 | (2011.01) |
| G05D 23/00 | (2006.01) |
| F27B 17/02 | (2006.01) |
| A61C 13/20 | (2006.01) |

(52) U.S. Cl.
CPC ............ *F27B 17/025* (2013.01); *A61C 13/20* (2013.01)

(58) Field of Classification Search
None
See application file for complete search history.

(56) References Cited

U.S. PATENT DOCUMENTS

| 5,997,293 | A | 12/1999 | Grünenfelder et al. |
| 2009/0224417 | A1* | 9/2009 | Lawton ................. B29C 33/308 |
| | | | 264/2.5 |
| 2011/0147968 | A1* | 6/2011 | Zubler ................. A61C 13/20 |
| | | | 264/16 |

FOREIGN PATENT DOCUMENTS

| CA | 2070691 A1 | 12/1992 |
| DE | 4119483 C2 | 6/1993 |
| DE | 19725866 C1 | 4/1999 |
| JP | 1-91852 A1 | 4/1989 |
| JP | 02-116366 A | 5/1990 |
| JP | 2000-329447 A1 | 11/2000 |

\* cited by examiner

*Primary Examiner* — Wissam Rashid
(74) *Attorney, Agent, or Firm* — Ann M. Knab; Thad McMurray

(57) ABSTRACT

A dental furnace having a display device and an operating device (10) for the dental furnace, is provided, the operating device being integrated in particular in the display device by forming a touch screen (12), and the operating device (10) facilitating the selection of programs for the firing of dental restoration parts in the dental furnace. The operating device (10) allows in particular the input of further parameters for a firing cycle. An operating element (30, 32, 34) facilitates the control of a final firing program of the dental furnace, namely with different values for the temperature as well as for the duration of the final firing, the operating element (30, 32, 34) making possible the simultaneous adjusting of temperature and duration parameters of the final firing.

13 Claims, 1 Drawing Sheet

DENTAL FURNACE HAVING A COMBINED DISPLAY AND OPERATING DEVICE

Figure 1:
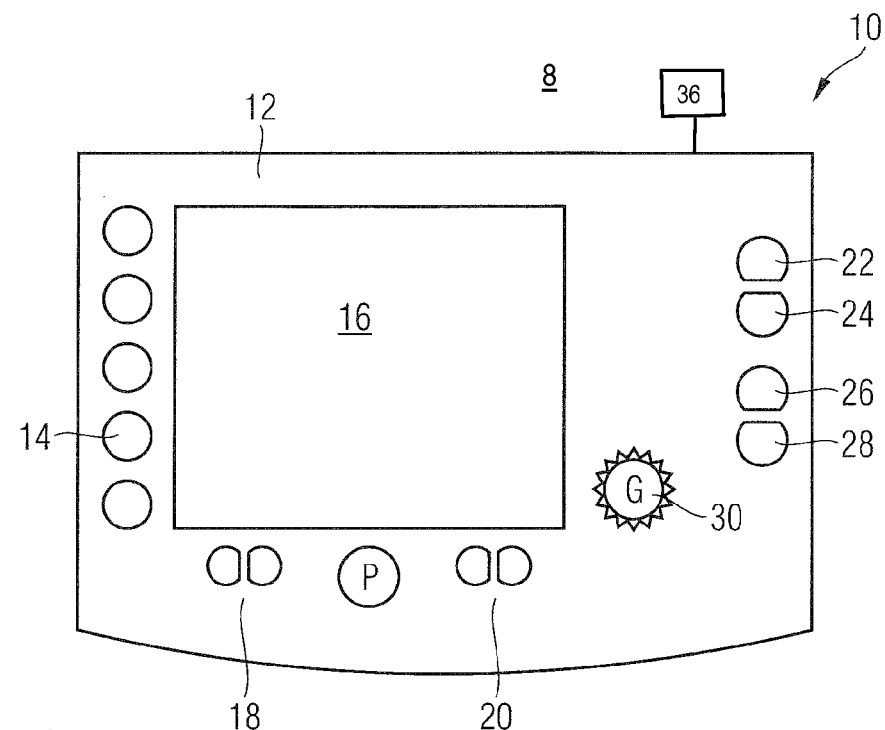

This application claims the benefit of German Patent Application Number 102013101633.2 filed Feb. 19, 2013, which is hereby incorporated by reference in its entirety.

The invention relates to a dental furnace having a display device and an operating device integrated in the display device by forming a touch screen, as well as to a method of operating a dental furnace in which the temperature and/or the selected program for the operation of the firing of dental restoration parts is set up on a display device, and wherein an operating device is used to adjust the program and/or further parameters of the dental furnace.

Ceramic dental materials are typically fired according to firing curves which are predefined precisely and with exact firing parameters. The setting of these firing parameters and of the firing curves is carried out in advance.

Dental furnaces of this type have been known for a long time and examples are described in DE 4 119 483 C2 and DE 19 725 866 C1 and corresponding U.S. Pat. No. 5,997,293, which are hereby incorporated by reference. In some cases the firing cycles are relatively varied and differ from one another regarding their type. As such, a distinction is made between oxidation firing, wash firing, dentine firing, incisal firing and glaze firing. In all firings, the firing parameters have to be complied with exactly according to the manufacturer's data for the corresponding material. This results in numerous programs, especially because typically a longer cycle time for the firing cycle has to be estimated for dental restoration parts with larger masses, such that for very large dental restoration parts, such as multi-unit bridges, the heating time and the cooling time increases.

Programs of this type are typically fixed programs in the dental furnace and can be changed by the operator to a very limited extent. Due to the plurality of fixed programs, the operation of the dental furnace becomes rather inconvenient, especially in the case of different materials which are to be fired. This complexity increases even further if the combination of the different above-mentioned firings is mandatory.

On the other hand, the prevailing view is such that successive firings typically influence one another such that it is preferred to have fixed combinations in order to meet the quality requirements of the dental restoration parts.

Especially in final firing or glaze firing, deviations are sometimes desired such that the firing parameters for final firing are typically freely adjustable and therefore the respective dental technician can decide on these parameters at his/her leisure. However, with unexperienced dental technicians this unfortunately leads to undesired results and can also result in a discarding of the entire dental restoration which has been fired repeatedly.

Contrary hereto, the invention is based on the task of providing a dental furnace, which makes possible an improved result especially when it comes to the final appearance of the dental restoration and offers a reduced dependence on the experience of the dental technician.

This task is inventively solved by the embodiments described in this application.

According to the invention, an operating element is provided which is basically independent of the setting of the specific programs. As a result, the complexity of the operation is reduced because there is no need to combine every possible arrangement of the final firing with the individual remaining firing programs. In this way, esthetic requirements can be easily taken into account without any losses of quality because the result is determined prior to final firing in terms of translucency and in terms of the strength of the dental restoration.

By means of the inventive, especially favorable, simultaneous setting of temperature and duration parameters of the final firing, the setting is simplified surprisingly considerably without any losses of quality. The presetting allows for a simultaneous and proportional or substantially proportional setting of these two parameters synchronously such that the dental technician can, for instance, increase or reduce the intensity of the final firing based on a default setting for the final firing of his/her choice, depending whether surfaces are desired which are highly or slightly reflective.

As final firing is typically carried out without additional glazing material, it is not required to apply any additional material which eliminates problems regarding dimensional accuracy.

According to the invention, it is favorable if, from the outset, the dental furnace is designed in such a way that final firing, depending on the previous firings, is only provided in a range which prevents any damage to the dental restoration part. In this way, operational reliability is increased which still makes possible a finer differentiation of the desired glaze firing or final firing when it comes to uncritical parameters of the respective dental restoration.

For instance, with a program which has been carried out in advance for a ten-unit bridge which requires a dental restoration of a respective volume and weight the permissible range for the temperature and duration parameter pairs of the final firing can be moved to higher ranges. This is stipulated by the control program of the dental furnace such that from the start the dental technician is provided with a standardized default within the desired final firing range.

For instance, the mean value of the default can be "100%", and the lower and higher values can be expressed as a percentage in an appropriate manner.

According to the invention it is also especially favorable if the remaining program parameters of the furnace, such as for a dentine firing or an incisal firing, are not displayed when turning on the final firing mode and cannot be changed anymore. This also draws the attention of the dental technician to the necessity of adjusting the final firing, for instance when he/she wants to deviate from a default setting of 100%.

It is also possible to organize the number of possible settings of the final firing parameter values in only a few stages, for instance "low", "medium" and "high". In relatively large dental laboratories it can be advantageous if the basic setting of the operational possibilities of the dental furnace can only be carried out by a leading hand or administrator and the executing dental technician is only provided with a limited choice in his/her operator mode. In this respect it is also possible to limit the choices for the final firing respectively.

In an advantageous embodiment of the invention, it is possible to allocate certain final firing settings to the executing dental technicians and to label them using markings. This enables the dental technician concerned to make a preferred final firing setting without further calculating.

It is also possible to assign these final firing settings to the respective user.

It is also possible to couple the respective final firing setting to a user administration and to preselect the respective final firing setting or offer it as a preselection as soon as the respective user has logged onto the dental furnace in order to still enable the user to make changes in individual cases.

Further advantages, details and features may be taken from the following description of one exemplary embodiment of the invention with reference to the drawings.

Figure 2:
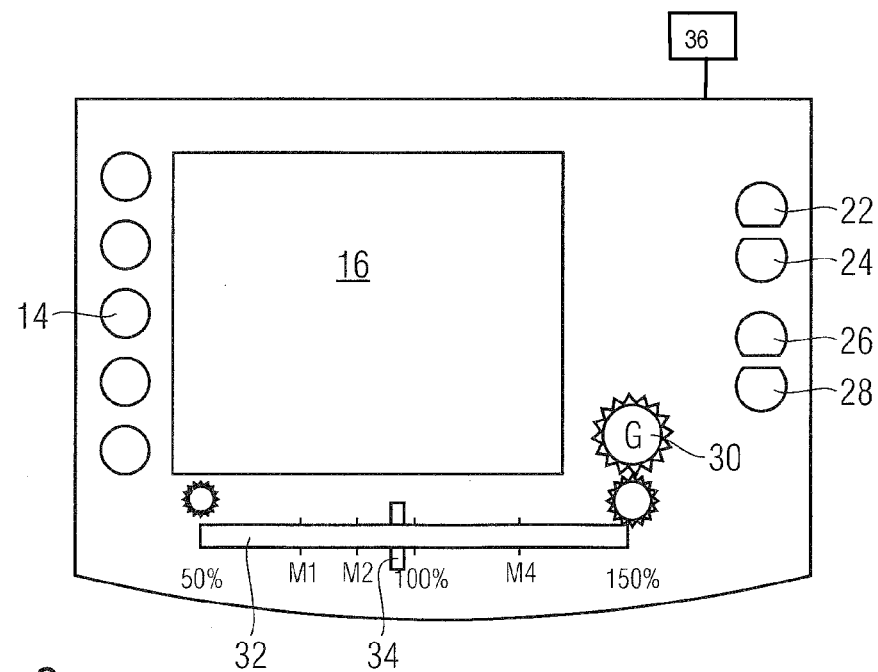

FIG. 1 shows a schematic view of a display device in combination with an operating device of an inventive dental furnace in one embodiment; in standard mode; and FIG. 2 shows the combined display and operating device according to FIG. 1, in the final firing mode.

In FIG. 1 a combined display and operating device 10 of an inventive dental furnace 8 is illustrated. The dental furnace 8 comprises a control device 36 which makes it possible to control firing cycles for dental restoration parts which are situated in the dental furnace in response to the input of program parameters via a key P of the display and operating device 10.

The display and operating device comprises a touch screen 12 which comprises panels, such as keys 14, which activate a function if each key is touched. The keys 14 and the remaining operating elements are disposed in a symbolic way only, as known per se, and the respective desired function is activated if touched.

Furthermore, the screen 12 comprises a display panel 16 which, depending on the running program, illustrates the firing curve undergone, the respective existing temperature at the respective existing measuring points of the dental furnace or the remaining firing time. The program function P can be operated via the auxiliary keys 18 and 20 wherein individual programs can be selected or changes of parameters can be carried out within the programs.

The furnace hood of the dental furnace can be opened and closed by keys 22 and 24 in order to make possible free access to the dental restoration part or to close the furnace and thus initiate the firing cycle.

Moreover, keys 26 and 28 are provided which are labelled "Stop" and "Start" and make it possible, for example, to start or end a firing cycle.

According to the invention, a key 30 is also provided which is assigned to a final firing function. By pressing this key the display and operating device 10 is changed in terms of its image content such that the image illustrated in FIG. 2 is produced. For instance, the display panel 16 will then show the existing temperature in the dental furnace. The key P and the associated auxiliary keys 18 and 20 are hidden and instead a slide control 32 pops up, which is associated with the final firing mode and makes it possible to adjust the intensity of the final firing.

For this purpose, the slide control 32 comprises a control 34 which moves along the slide control 32 at the touch of a finger in order to adjust the desired intensity of the final firing in this way. The key 30, the slide control 32 and the control 34 together form an operating element for the final firing.

In the exemplary embodiment illustrated, the slide control 32 comprises markings which are supposed to symbolize the possible adjusting range. The leftmost marking is, for instance, 50% and the rightmost marking is, for instance, 150% and it is to be understood that instead any other values, such as in the range of 30% to 300%, can be realized.

In one embodiment, the control device 36 for the dental furnace responding to the operating element (30, 32, 34) for controlling the final firing program includes a preset mode in which a temperature and a duration are preset for a predefined final firing value, and wherein the temperature and duration increase in a monotonous way with increasing final firing values. In monotonic or monotonous curves, the successive members of sequences either consistently increase or decrease but do not oscillate in relative value. Each member of a monotone increasing sequence is greater than or equal to the preceding member; each member of a monotone decreasing sequence is less than or equal to the preceding member.

After adjusting the desired final firing value via the control 34, the key 30 is again touched lightly and thus the final firing is started. The final firing is carried out in this condition, and the slide control is illustrated in a darkened manner in order to show that no more changes can be made to the adjusted parameters once the final firing has been started.

Instead of lightly touching the key 30 again, the start key 28 can be activated and the respective function can be started.

The markings M1, M2 and M4 correspond to the preferred positions of the control 32 for the users M1, M2 and M4.

The display panel 16 shows when the final firing has been finished and the dental technician can, possibly after expiration of a holding time or time of day, remove the finished dental restoration part(s) after opening the furnace via the key 22.

If the dental furnace is not opened between the end of a firing program via key P and the activation of the final firing function via key 30, the control device of the dental furnace assumes that it must be the same dental restoration part. Its mass and type which have been determined and confirmed earlier can be introduced to the translucency of the final firing mode such that a presetting can be implemented according to the dental restoration part which is to be fired by final firing now.

However, if final firing is started after the dental furnace has been opened, a final firing default setting is assumed which can be changed obviously via the slide control 32.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

The invention claimed is:

1. A dental furnace comprising
   a display device and
   an operating device,
   wherein the operating device is integrated in the display device by forming a touch screen,
   wherein the operating device facilitates the selection of programs for the firing of dental restoration parts in the dental furnace,
   wherein the operating device allows the input of further parameters for a firing cycle,
   wherein an operating element facilitates the control of a final firing program of the dental furnace, with different values for the temperature as well as for the duration of the final firing,
   the operating element causing the simultaneous adjusting of temperature and duration of time parameters of the final firing,
   wherein the operating element is connected to a control device for the final firing program, and
   wherein the control device adjusts the temperature and duration of the final firing and increases the duration as the temperature increases.

2. The dental furnace according to claim 1, wherein a control device of the dental furnace allows the activation of a final firing program with a plurality of values for temperature and duration of the final firing, wherein the temperature as well as the duration of the final firing are increased with increased values and reduced with reduced values.

3. The dental furnace according to claim 1, wherein a control device for the dental furnace responding to the operating element for controlling the final firing program comprises a preset mode in which a temperature and a duration are preset for a predefined final firing value, and wherein the temperature and duration consistently increase without oscillating with increasing final firing values.

4. The dental furnace according to claim 1, wherein the operating panel comprises a slide control function by which the intensity of the final firing is adjustable, and wherein a predefined final firing value of the slide control is adjustable by an operator.

5. The dental furnace according to claim 1, wherein the display device is integrated in the operating device of the dental furnace in the form of a touch screen and comprises a key function which activates a final firing program and which displays an adjustable final firing control on the display device.

6. The dental furnace according to claim 5, wherein the operating panel of the final firing program offers at least 2 values for adjusting the final firing program which each comprise predefined and allocated settings for the temperature and duration of the final firing.

7. The dental furnace according to claim 1, wherein temperature/time value pairs are preset for the final firing and provide a plurality of value pairs to the user for adjusting the final firing.

8. The dental furnace of claim 1 wherein the operating element comprises an operating panel.

9. The dental furnace according to claim 8, wherein by activation of the operating panel for controlling a final firing program the display of the display device is changed in such a way that the parameter values of the final firing are adjustable.

10. The dental furnace according to claim 9, wherein in a final firing mode a remaining selection of programs for firing dental restoration parts is blocked.

11. The dental furnace according to claim 8, wherein the operating panel of the final firing program offers at least 3 values for adjusting the final firing program which each comprise predefined and allocated settings for the temperature and duration of the final firing.

12. The dental furnace according to claim 1, wherein temperature/time value pairs are preset for the final firing and provide 3 to 10 value pairs to the user for adjusting the final firing.

13. A method of operating a dental furnace, in which the temperature and/or the selected program for the operation of the firing of dental restoration parts is set up on a display device, and wherein an operating device is used to adjust the program and/or further parameters of the dental furnace, comprising:
  firing dental restoration parts,
  wherein after the firing of the dental restoration parts a final firing program of the dental furnace is selected via an operating element, and
  wherein one additional value from a predefined value pair comprising temperature and duration of the final firing is selected by which the temperature and the duration parameters of the final firing are adjusted simultaneously,
  wherein the temperature and duration of the final firing are adjusted such that the duration increases as the temperature increases.

* * * * *